(12) United States Patent
Yoshida et al.

(10) Patent No.: US 9,719,958 B2
(45) Date of Patent: Aug. 1, 2017

(54) GAS SENSOR CONTROLLER, GAS SENSOR SYSTEM, AND DETERIORATION DETERMINATION METHOD FOR GAS SENSOR ELEMENT

(71) Applicant: NGK SPARK PLUG CO., LTD., Nagoya-shi, Aichi (JP)

(72) Inventors: Akihiro Yoshida, Dusseldorf (DE); Kenji Kato, Nagoya (JP); Koji Shiotani, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 381 days.

(21) Appl. No.: 14/319,067

(22) Filed: Jun. 30, 2014

(65) Prior Publication Data
US 2015/0377822 A1    Dec. 31, 2015

(51) Int. Cl.
G01N 27/409    (2006.01)
G01N 27/419    (2006.01)

(52) U.S. Cl.
CPC ......... *G01N 27/409* (2013.01); *G01N 27/419* (2013.01)

(58) Field of Classification Search
CPC .. G01N 27/419; G01N 27/409; G01N 27/417; G01N 33/0037
See application file for complete search history.

(56) References Cited

U.S. PATENT DOCUMENTS

| 2007/0119708 A1* | 5/2007 | Oya | ................... G01N 27/4175 204/401 |
| 2009/0164091 A1 | 6/2009 | Kobayashi et al. | |

* cited by examiner

*Primary Examiner* — Gurpreet Kaur
(74) *Attorney, Agent, or Firm* — Sughrue Mion, PLLC

(57) ABSTRACT

A gas sensor controller (100) controls a gas sensor element (10) which has a first pump cell (111), a second pump cell (113), and an oxygen concentration detection cell (112). The controller includes first chamber control means (51) to (53) which pumps oxygen out of or into a first measurement chamber MR1 such that a concentration voltage Vs becomes equal to a target voltage Vr; target voltage changing means S72, S75 which changes the target voltage Vr from a first target voltage Vr1 to a second target voltage Vr2; current detection means (55) which detects the magnitude of a concentration current Ip2 flowing between first electrode (145) and second electrode (147); and deterioration determination means S7 which determines the deterioration state of the gas sensor element from a change which occurs in the concentration current Ip2 due to the change in the target voltage Vr.

9 Claims, 6 Drawing Sheets

GAS SENSOR CONTROLLER, GAS SENSOR SYSTEM, AND DETERIORATION DETERMINATION METHOD FOR GAS SENSOR ELEMENT

BACKGROUND OF THE INVENTION

1. Field of the Invention

The present invention relates to a gas sensor controller for controlling a gas sensor element which detects the concentration of a specific gas, a gas sensor system which includes the gas sensor controller and a gas sensor, and a deterioration determination method for determining the deterioration state of the gas sensor element.

2. Description of the Related Art

Conventionally, a gas sensor has been known which includes a gas sensor element for detecting the concentration of a specific gas contained in, for example, the exhaust gas of an internal combustion engine, and a gas sensor controller for controlling the gas sensor element. For example, Patent Document 1 discloses an NOx sensor which includes a gas sensor element (NOx sensor element) for detecting nitrogen oxides (NOx) as a specific gas, and a gas sensor controller which controls the gas sensor element and calculates the concentration of nitrogen oxides contained in an object gas.

Notably, the NOx sensor element used in the NOx sensor has first and second measurement chambers which respectively have a first pump cell and a second pump cell each formed of a solid electrolyte body.

The object gas is introduced into the first measurement chamber, and the first pump cell controls the first chamber gas within the first measurement chamber to a predetermined oxygen concentration. One of the paired electrodes of the second pump cell is disposed in the second measurement chamber. When a predetermined voltage is applied to the second pump cell, oxygen molecules and oxygen-containing gas molecules including oxygen atoms in their respective structures (e.g., NOx) introduced into the second measurement chamber from the first measurement chamber are disassociated. As a result, a concentration current corresponding to the concentration of the oxygen molecules and oxygen-containing gas molecules contained in the second chamber gas flows between the electrodes of the second pump cell. Therefore, the gas sensor controller can detect the concentration of the oxygen-containing gas from the magnitude of the concentration current flowing between the electrodes of the second pump cell.

[Patent Document 1] U.S. Patent Application Laid-Open No. 2009/0164091

3. Problem to be Solved by the Invention

When the gas sensor element used in such a gas sensor deteriorates due to use or other causes, it has been found that the response of the sensor becomes slow. For example, an NOx sensor must have a good response characteristic in order to cope with recent strict NOx regulations. However, if the response of the sensor becomes slow due to deterioration of an NOx sensor element used in the NOx sensor, the NOx sensor may fail to satisfy the required response characteristic. Therefore, there has been a demand for a gas sensor controller which can determine the deterioration state of such a gas sensor element whose response has become slow.

SUMMARY OF THE INVENTION

The present invention has been accomplished to solve the above problem. It is therefore an object of the present invention to provide a gas sensor controller which can determine the deterioration state of a gas sensor element, a gas sensor system which includes such a gas sensor controller and a gas sensor, and a deterioration determination method for determining the deterioration state of the gas sensor element.

The above object has been achieved in a first aspect of the invention by providing (i) a gas sensor controller for controlling a gas sensor element having a first measurement chamber into which an external object gas is introduced and a second measurement chamber which communicates with the first measurement chamber and into which a first chamber gas within the first measurement chamber is introduced, the gas sensor element comprising a first pump cell which is formed of a first solid electrolyte body and which pumps oxygen out of the first chamber gas within the first measurement chamber or pumps oxygen into the first measurement chamber; a second pump cell which is formed of a second solid electrolyte body and which has first and second electrodes formed on the second solid electrolyte body such that the first electrode is located in the second measurement chamber and the second electrode is located outside the second measurement chamber; and an oxygen concentration detection cell which is formed of a third solid electrolyte body and which has detection and reference electrodes formed on the third solid electrolyte body such that the detection electrode is located in the first measurement chamber and the reference electrode is exposed to an atmosphere having a reference oxygen concentration. The gas sensor controller comprises first chamber control means for pumping oxygen out of the first measurement chamber or pumping oxygen into the first measurement chamber by operating the first pump cell such that a concentration voltage generated between the detection electrode and the reference electrode of the oxygen concentration detection cell becomes equal to a target voltage; target voltage changing means for changing the target voltage from a first target voltage to a second target voltage different from the first target voltage; current detection means for detecting the magnitude of a concentration current which flows between the first electrode and the second electrode in accordance with the concentration of oxygen molecules and oxygen-containing gas molecules having a dissociation voltage higher than that of oxygen molecules, the oxygen molecules and the oxygen-containing gas molecules being contained in a second chamber gas within the second measurement chamber; and deterioration determination means for determining a deterioration state of the gas sensor element from a change which occurs in the concentration current as a result of the target voltage for the concentration voltage being changed by the target voltage changing means.

In the gas sensor controller (1), the first chamber control means pumps oxygen out of or into the first measurement chamber by operating the first pump cell such that the concentration voltage generated between the electrodes of the oxygen concentration detection cell becomes equal to a target voltage. Meanwhile, the target voltage changing means changes the target voltage for the concentration voltage from a first target voltage to a second target voltage. Further, the current detection means detects the magnitude of the concentration current which flows between the first electrode and the second electrode of the second pump cell. When the target voltage for the concentration voltage is changed, the oxygen concentration of the first chamber gas changes, and the concentration of the oxygen molecules and oxygen-containing gas contained in the second chamber gas within the second measurement chamber also changes.

Therefore, the magnitude of the detected concentration current also changes. Meanwhile, the manner of change of the concentration current changes with the degree of deterioration of the gas sensor element. Based thereon, the deterioration determination means determines the deterioration state of the gas sensor element from a change which occurs in the concentration current due to the change in the target voltage. Thus, the deterioration state of the gas sensor element can be determined.

Notably, the oxygen-containing gas molecules having a dissociation voltage higher than that of oxygen molecules are oxygen-containing gas molecules which contain oxygen atoms in their respective structures and have a dissociation voltage higher than that of oxygen molecules ($O_2$). Examples of the oxygen-containing gas molecules include nitrogen oxide (NOx), CO, and $H_2O$ gas.

No limitation is imposed on the first target voltage and the second target voltage so long as they differ from each other. However, preferably, one of the first and second target voltages is set to a value which is maintained when the gas sensor controller measures the concentration of the oxygen-containing gas contained in the object gas, and the other target voltage is set to a voltage higher or lower than the one target voltage.

Also, in the gas sensor controller (1), the oxygen concentration of the first chamber gas is changed by changing the target voltage for the concentration voltage from the first target voltage to the second target voltage. Thus, a change in the concentration current can be obtained, and the deterioration state of the gas sensor element can be determined.

Examples of the method of changing the target voltage from the first target voltage to the second target voltage include a method of increasing the target voltage rampwise from the first target voltage to the second target voltage, and a method of decreasing the target voltage rampwise from the first target voltage to the second target voltage. Other examples of the method of changing the target voltage from the first target voltage to the second target voltage include a method of changing the target voltage to exhibit an S-shaped change such that its change rate becomes small at the beginning and end of the change, a method of changing the target voltage instantaneously, and a method of changing the target voltage stepwise with elapse of time. Also, the period of the change from the first target voltage to the second target voltage may be freely changed.

In a preferred embodiment (2) of the gas sensor controller (1), the target voltage changing means gradually changes the target voltage from the first target voltage to the second target voltage such that the concentration current does not overshoot.

In the gas sensor controller (2), the target voltage is changed gradually such that the concentration current does not overshoot. Therefore, a change in the concentration current corresponding to the deterioration state of the gas sensor element can be obtained properly. Notably, examples of the manner of changing the target voltage include changing the target voltage rampwise and changing the target voltage stepwise with elapse of time.

In another preferred embodiment (3) of the above-described gas sensor controllers (1) or (2), in the case where the second target voltage is lower than the first target voltage, and the concentration current increases from a first concentration current to a second concentration current as a result of the target voltage being changed from the first target voltage to the second target voltage by the target voltage changing means, the deterioration determination means determines the deterioration state of the gas sensor element based on an index which relates to the change occurring in the concentration current and reflects the length of a period needed for the concentration current to approach the second concentration current.

In the gas sensor controller (3), the target voltage changing means changes the target voltage from the first target voltage to a second target voltage lower than that of the first target voltage. As a result, the concentration current increases from the first concentration current at the first target voltage to the second concentration current at the second target voltage. Incidentally, it has been found that, of changes which occur in the concentration current, the period during which the concentration current approaches the second concentration current (in other words, the period during which the rate of increase of the concentration current decreases gradually and the concentration current converges to (reaches) the second concentration current) increases in length with the degree of deterioration of the gas sensor element, and a difference in the length of this period due to a difference in the degree of deterioration is appreciable. In view of the above, the deterioration determination means determines the deterioration state of the gas sensor element based on an index which relates to the change occurring in the concentration current and which reflects the length of a period needed for the concentration current to approach the second concentration current.

Thus, the deterioration state of the gas sensor element can be suitably determined by using an index which reflects the length of the period needed for the concentration current to approach the second concentration current.

Examples of such an index include a response time described below which is needed for the concentration current to change from 10% of the second concentration current to 90% thereof (a response time Tr in FIG. 3) and the magnitude of the concentration current at a predetermined time during the period during which the concentration current approaches the second concentration current.

In a second aspect (4), the present invention provides a gas sensor system which includes any of the above-described gas sensor controllers (1)-(3) and a gas sensor including the gas sensor element and which is mounted on a vehicle, wherein the deterioration determination means of the gas sensor controller determines the deterioration state of the gas sensor element after an engine of the vehicle is stopped.

In this gas sensor system, the deterioration state of the gas sensor element mounted on the vehicle can be suitably determined. Also, since the deterioration state of the gas sensor element is determined by the deterioration determination means after the engine of the vehicle is stopped, the determination of the deterioration state does not hinder measurement of the concentration of the oxygen-containing gas by the gas sensor during normal operation.

In yet another aspect (5), the present invention provides a deterioration determination method for determining a deterioration state of a gas sensor element having a first measurement chamber into which an external object gas is introduced and a second measurement chamber which communicates with the first measurement chamber and into which a first chamber gas within the first measurement chamber is introduced, the gas sensor element comprising a first pump cell which is formed of a first solid electrolyte body and which pumps oxygen out of the first chamber gas within the first measurement chamber or pumps oxygen into the first measurement chamber; a second pump cell which is formed of a second solid electrolyte body and which has first and second electrodes formed on the second solid electrolyte body such that the first electrode is located in the second measurement chamber and the second electrode is located outside the second measurement chamber; and an oxygen concentration detection cell which is formed of a third solid electrolyte body and which has detection and reference electrodes formed on the third solid electrolyte body such that the detection electrode is located in the first measurement chamber and the reference electrode is exposed to an atmosphere having a reference oxygen concentration. The method comprises the steps of creating a state in which oxygen is pumped out of the first measurement chamber or is pumped into the first measurement chamber by the first pump cell such that a concentration voltage generated between the detection electrode and the reference electrode of the oxygen concentration detection cell becomes equal to a target voltage which is set to a first target voltage; changing the target voltage from the first target voltage to a second target voltage different from the first target voltage; detecting a concentration current which flows between the first electrode and the second electrode in accordance with the concentration of oxygen molecules and oxygen-containing gas molecules having a dissociation voltage higher than that of oxygen molecules, the oxygen molecules and the oxygen-containing gas being contained in a second chamber gas within the second measurement chamber; and determining the deterioration state of the gas sensor element from a change which occurs in the concentration current as a result of a change in the target voltage.

As described above, a change in the concentration current which occurs due to a change in the target voltage for the concentration voltage (specifically, the period during which the concentration current approaches a predetermined current value) changes with the degree of deterioration of the gas sensor element. Therefore, the above-described deterioration determination method can properly determine the deterioration state of the gas sensor element.

DESCRIPTION OF REFERENCE SYMBOLS

Figure 1:
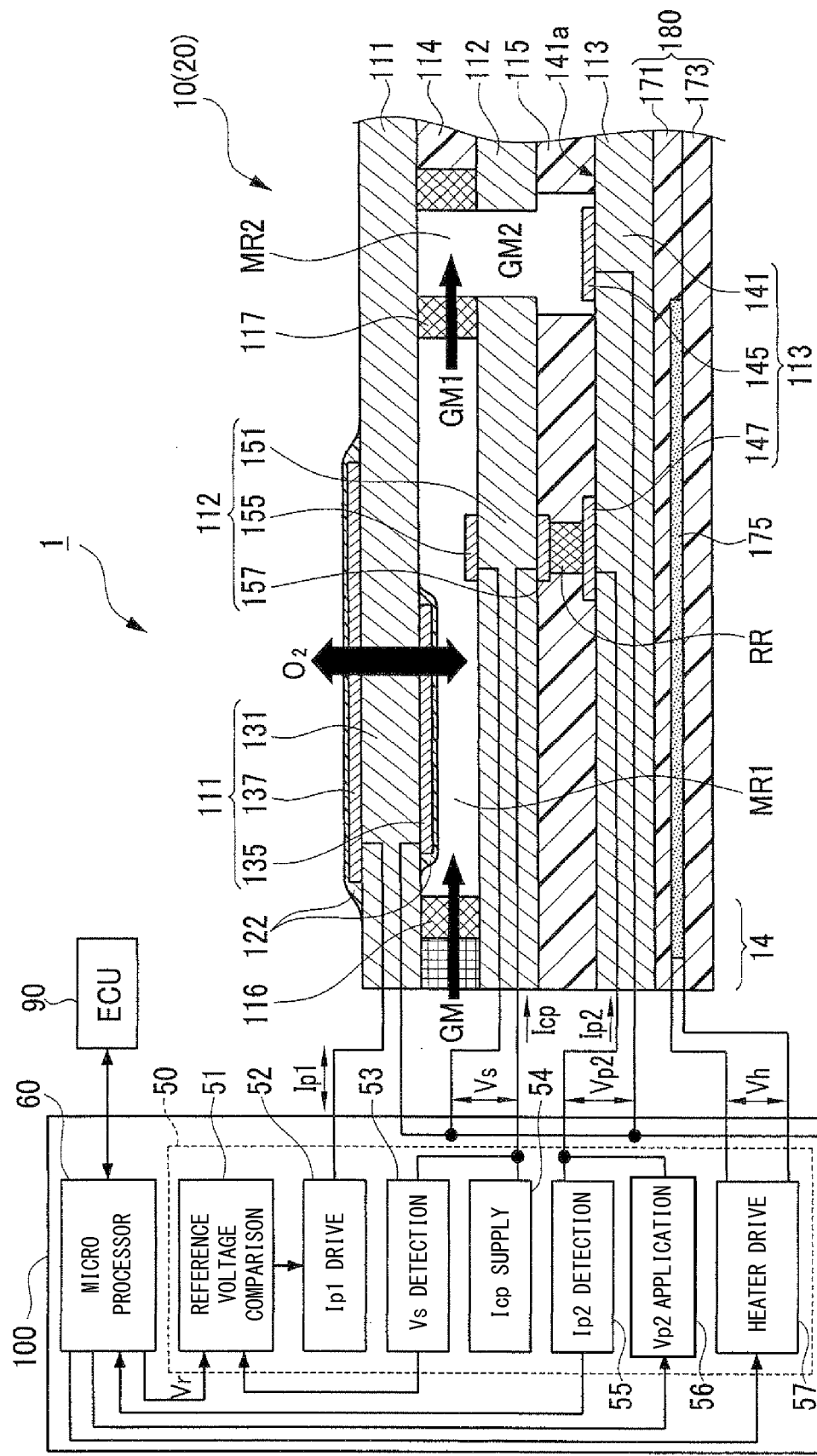
FIG. 1 schematically shows the configuration of an NOx sensor system (gas sensor system) which includes a gas sensor controller according to an embodiment and an NOx sensor including an NOx sensor element.

Reference symbols used to identify various features in the drawings including the following.
1: NOx sensor system (gas sensor system)
10: NOx sensor element (gas sensor element)
20: NOx sensor (gas sensor)
111: first pump cell
131: first solid electrolyte layer
135: first-pump-dedicated first electrode
137: first-pump-dedicated second electrode
112: oxygen concentration detection cell
151: third solid electrolyte layer
155: detection electrode
157: reference electrode
113: second pump cell
141: second solid electrolyte layer
145: second-pump-dedicated first electrode (first electrode)
147: second-pump-dedicated second electrode (second electrode)
116: first diffusion resistor
117: second diffusion resistor
RR: reference oxygen chamber
MR1: first measurement chamber
MR2: second measurement chamber
180: heater section
GM: exhaust gas (object gas)
GM1: first chamber gas
GM2: second chamber gas
100: gas sensor controller
50: electric circuit section
51: reference voltage comparison circuit (first chamber control means)
52: Ip1 drive circuit (first chamber control means)
53: Vs detection circuit (first chamber control means)
54: Icp supply circuit
55: Ip2 detection circuit (current detection means)
56: Vp2 application circuit
57: heater drive circuit
60: microprocessor
Vs: concentration detection voltage (concentration voltage)
Vp2: second pump voltage
Ip2: second pump current (concentration current)
Tr: response time
S7: deterioration determination means
S72, S75: target voltage changing means
S73, S76: current detection means

DETAILED DESCRIPTION OF THE PREFERRED EMBODIMENTS

An embodiment of the present invention will now be described with reference to the drawings. However, the present invention should not be construed as being limited thereto.

FIG. 1 is an explanatory diagram schematically showing the configuration of an NOx sensor system 1 (gas sensor system) which includes a gas sensor controller 100 according to the present embodiment and an NOx sensor 20 including an NOx sensor element 10.

The NOx sensor system 1 is mounted on a vehicle (not shown) which includes an unillustrated internal combustion engine (hereinafter, also referred to as the engine). The NOx sensor system 1 detects the NOx concentration of exhaust gas GM (object gas) of the engine by controlling the NOx sensor element 10 (NOx sensor 20) using the gas sensor controller 100. The NOx sensor 20 is composed of the NOx sensor element 10 and an unillustrated metallic shell which accommodates the NOx sensor element 10.

Notably, in the following description, the left side of FIG. 1 will be referred to as the front end side of the NOx sensor element 10, and the right side of FIG. 1 will be referred to as the rear end side of the NOx sensor element 10.

First, the NOx sensor element 10 of the NOx sensor 20 will be described.

The NOx sensor element 10 has a structure in which a first pump cell 111, an oxygen concentration detection cell 112, and a second pump cell 113 are stacked, with insulating layers 114 and 115 mainly formed of alumina being interposed therebetween. A heater section 180 is stacked on the side of the NOx sensor element 10 where the second pump cell 113 is located.

The first pump cell 111 is composed of a first solid electrolyte layer 131 (solid electrolyte body mainly formed of zirconia) and a first-pump-dedicated first electrode 135 and a first-pump-dedicated second electrode 137 which are porous and are disposed to sandwich the first solid electrolyte layer 131. The first-pump-dedicated first electrode 135 is disposed to face a first measurement chamber MR1 described below. The surfaces of the first-pump-dedicated first and second electrodes 135 and 137 are covered with protection layers 122 each formed of a porous material.

The oxygen concentration detection cell 112 is composed of a third electrolyte layer 151 (solid electrolyte body mainly formed of zirconia) and a detection electrode 155 and a reference electrode 157 which are porous and are disposed to sandwich the third solid electrolyte layer 151.

The second pump cell 113 is composed of a second solid electrolyte layer 141 (solid electrolyte body mainly formed of zirconia) and a second-pump-dedicated first electrode 145 and a second-pump-dedicated second electrode 147 which are porous and are disposed on the surface 141a of the second solid electrolyte layer 141 which faces the insulating layer 115.

The NOx sensor element 10 has the first measurement chamber MR1 formed therein. An external exhaust gas GM is introduced into this first measurement chamber MR1 through a first diffusion resistor 116 disposed between the first pump cell 111 and the oxygen concentration detection cell 112.

The first diffusion resistor 116 is formed of a porous material and is disposed in an introduction passage 14 for the exhaust gas GM which extends from an opening of the NOx sensor element 10 at the front end side (left side in the drawing) thereof to the first measurement chamber MR1. Thus, the first diffusion resistor 116 restricts the introduction amount of the exhaust gas GM to the first measurement chamber MR1 per unit time.

The NOx sensor element 10 also has a second diffusion resistor 117 which is formed of a porous material and which is disposed on the rear end side (right side in the drawing) of the first measurement chamber MR1. Further, a second measurement chamber MR2 is formed on the rear end side of the second diffusion resistor 117. The first chamber gas GM1 within the first measurement chamber MR1 is introduced into the second measurement chamber MR2 through the second diffusion resistor 117. The second measurement chamber MR2 is formed such that it penetrates the insulating layers 114 and 115 and the oxygen concentration detection cell 112 in the stacking direction. The second-pump-dedicated first electrode 145 of the second pump cell 113 faces the second measurement chamber MR2.

The NOx sensor element 10 has a reference oxygen chamber RR which is formed between the third solid electrolyte layer 151 of the oxygen concentration detection cell 112 and the second solid electrolyte layer 141 of the second pump cell 113. This reference oxygen chamber RR is surrounded by the third solid electrolyte layer 151 of the oxygen concentration detection cell 112, the second solid electrolyte layer 141 of the second pump cell 113, and the insulating layer 115. The reference electrode 157 of the oxygen concentration detection cell 112 and the second-pump-dedicated second electrode 147 of the second pump cell 113 are disposed to face the reference oxygen chamber RR.

The heater section 180 is constituted by stacking sheet-shaped insulating layers 171 and 173 formed of insulating ceramic such as alumina. The heater section 180 includes a heater pattern 175 disposed between the insulating layers 171 and 173. When current is caused to flow through the heater pattern 175 (upon application of voltage Vh), the heater section 180 generates heat.

Next, the gas sensor controller 100 will be described.

The gas sensor controller 100 is mainly composed of a microprocessor 60 and an electric circuit section 50. The electric circuit section 50 is electrically connected to the NOx sensor element 10 of the NOx sensor 20. The microprocessor 60 is connected to an ECU 90. In accordance with an instruction from the ECU 90, the microprocessor 60 of the gas sensor controller 100 drives and controls the NOx sensor element 10, and detects the concentration of NOx contained in the exhaust gas.

The electric circuit section 50 includes a reference voltage comparison circuit 51, an Ip1 drive circuit 52, a Vs detection circuit 53, an Icp supply circuit 54, an Ip2 detection circuit 55, a Vp2 application circuit 56, and a heater drive circuit 57.

The Icp supply circuit 54 supplies a very small current Icp between the detection electrode 155 and the reference electrode 157 of the oxygen concentration detection cell 112. As a result, oxygen is pumped out from the first measurement chamber MR1 into the oxygen reference chamber RR, whereby an atmosphere having a predetermined oxygen concentration can be created in the reference oxygen chamber RR.

The Vs detection circuit 53 detects a concentration detection voltage Vs between the detection electrode 155 and the reference electrode 157 of the oxygen concentration detection cell 112, and outputs the detected concentration detection voltage Vs to the reference voltage comparison circuit 51.

The reference voltage comparison circuit 51 compares the concentration detection voltage Vs detected by the Vs detection circuit 53 with a predetermined target voltage Vr (e.g., 425 mV) output from the microprocessor 60, and outputs the comparison result to the Ip1 drive circuit 52.

The Ip1 drive circuit 52 supplies a first pump current Ip1 between the first-pump-dedicated first electrode 135 and the first-pump-dedicated second electrode 137 of the first pump cell 111, and controls the magnitude and direction of the first pump current Ip1 based on the result of the comparison by the reference voltage comparison circuit 51 such that the concentration detection voltage Vs coincides with the target voltage Vr. As a result, at the first pump cell 111, oxygen is pumped out of the first measurement chamber MR1 to the exterior of the NOx sensor element 10, or oxygen is pumped from the exterior of the NOx sensor element 10 into the first measurement chamber MR1.

As a result of the above-described control, the first pump current Ip1 flowing through the first pump cell 111 is controlled such that the concentration detection voltage Vs between the detection electrode 155 and the reference electrode 157 of the oxygen concentration detection cell 112 becomes equal to the predetermined target voltage Vr, whereby the oxygen concentration of the first chamber gas GM1 within the first measurement chamber MR1 is controlled to a predetermined concentration.

The first chamber gas GM1 controlled to the predetermined concentration is introduced into the second measurement chamber MR2 through the porous second diffusion resistor 117.

The Vp2 application circuit 56 applies a second pump voltage Vp2 (e.g., 450 mV) between the second-pump-dedicated first and second electrode 145 and 147 of the second pump cell 113. By applying the second pump voltage Vp2, oxygen molecules and NOx (oxygen-containing gas molecules) having a dissociation voltage higher than that of oxygen molecules which are contained in the second chamber gas GM2 within the second measurement chamber MR2 are dissociated.

As a result, in the second measurement chamber MR2, the oxygen and NOx contained in the second chamber gas GM2 within the second measurement chamber MR2 are dissociated by the catalytic action of the second-pump-dedicated first electrode 145 of the second pump cell 113, and oxygen ions produced as a result of the dissociation move through the second solid electrolyte layer 141, whereby a second pump current Ip2 flows between the second-pump-dedicated first electrode 145 and the second-pump-dedicated second electrode 147.

The Ip2 detection circuit 55 detects the magnitude of the second pump current Ip2 flowing between the second-pump-dedicated first electrode 145 and the second-pump-dedicated second electrode 147.

The heater drive circuit 57, which is controlled by the microprocessor 60, controls the supply of electric current to the heater pattern 175 of the heater section 180, to thereby cause the heater section 180 to generate heat. As a result, the first solid electrolyte layer 131 of the first pump cell 111, the third solid electrolyte layer 151 of the oxygen concentration detection cell 112, and the second solid electrolyte layer 141 of the second pump cell 113 are heated to an activation temperature (e.g., 750° C.).

In the above-described configuration, the NOx sensor element 10 is controlled by the gas sensor controller 100, whereby the concentration of NOx contained in the exhaust gas is detected from the magnitude of the second pump current Ip2.

However, when the NOx sensor element 10 deteriorates due to use or other causes, the response of the NOx sensor element 10 becomes slow. Therefore, due to deterioration of the NOx sensor element 10, the NOx sensor may fail to satisfy the requisite response characteristic. Therefore, the present gas sensor controller 100 includes means for determining the deterioration state of the NOx sensor element 10 whose response has become slow.

Figure 2:
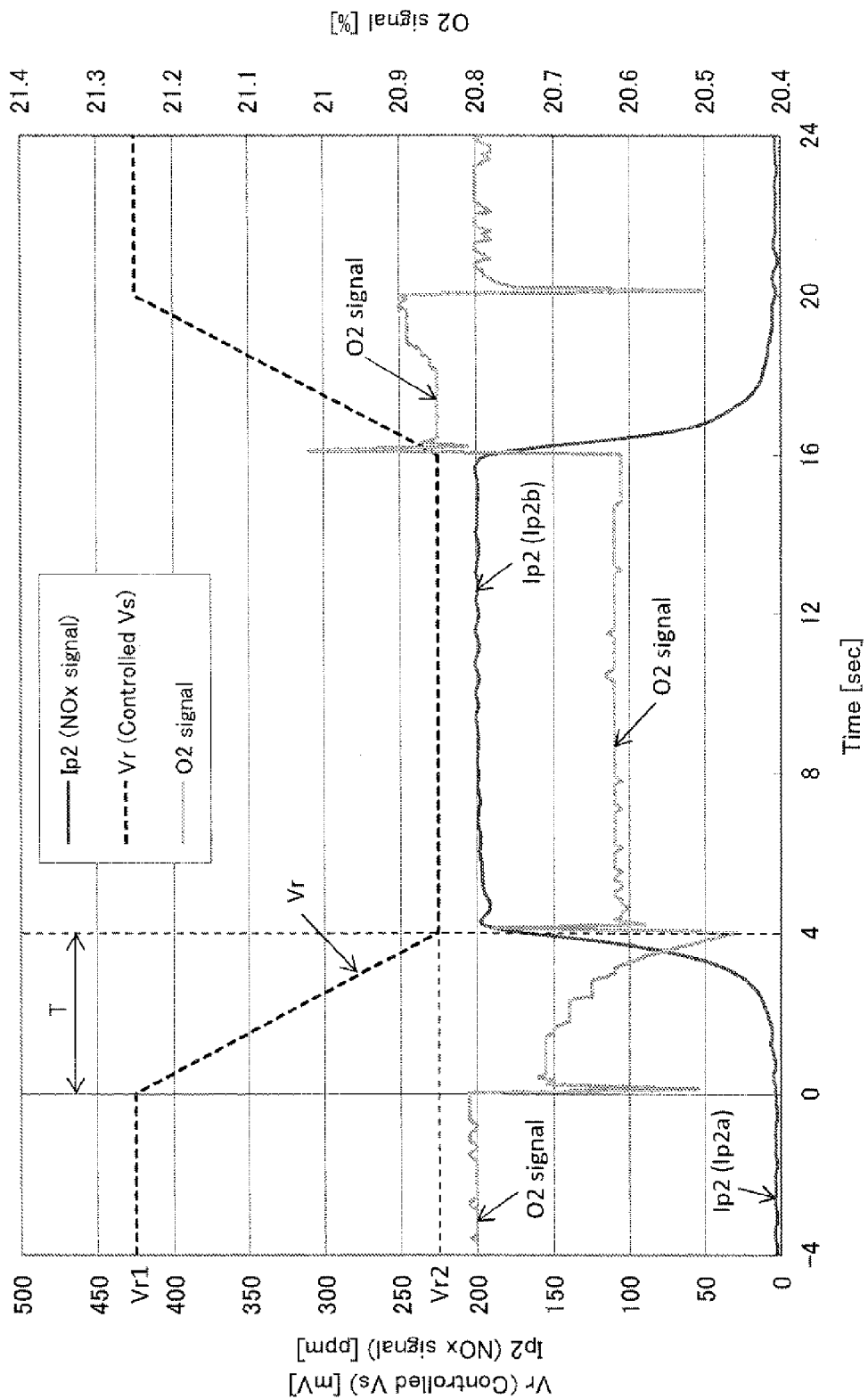
FIG. 2 is a graph showing the second pump current and oxygen concentration signal response with a change in target voltage.

Specifically, in the gas sensor controller 100 of the present embodiment, the target voltage Vr which is output from the microprocessor 60 to be compared with the concentration detection voltage Vs in the reference voltage comparison circuit 51 is changed from a first target voltage Vr1 (=425 mV) for detecting NOx concentration to a second target voltage Vr2 (=225 mV) lower than the first target voltage Vr1, as shown by a broken line in FIG. 2. Thus, the oxygen concentration of the first chamber gas GM1 is changed. Further, in the present embodiment, when the target voltage Vr is changed from the first target voltage Vr1 to the second target voltage Vr2, the target voltage Vr is changed rampwise over a predetermined period of time T (T=4 sec in the present embodiment).

Notably, the vertical axis on the left side of FIG. 2 represents not only the voltage value (unit: mV) of the target voltage Vr indicated by a broken line, but also the magnitude of the second pump current Ip2 indicated by a dark continuous line. The magnitude of the second pump current Ip2 is represented by NOx concentration (unit: ppm) converted therefrom. The vertical axis on the right side of FIG. 2 represents the oxygen concentration (unit: %) of the exhaust gas GM indicated by a pale continuous line. The horizontal axis represents time t (unit: sec) elapsed from a reference timing at which the target voltage Vr has started to change (t=0).

Figure 3:
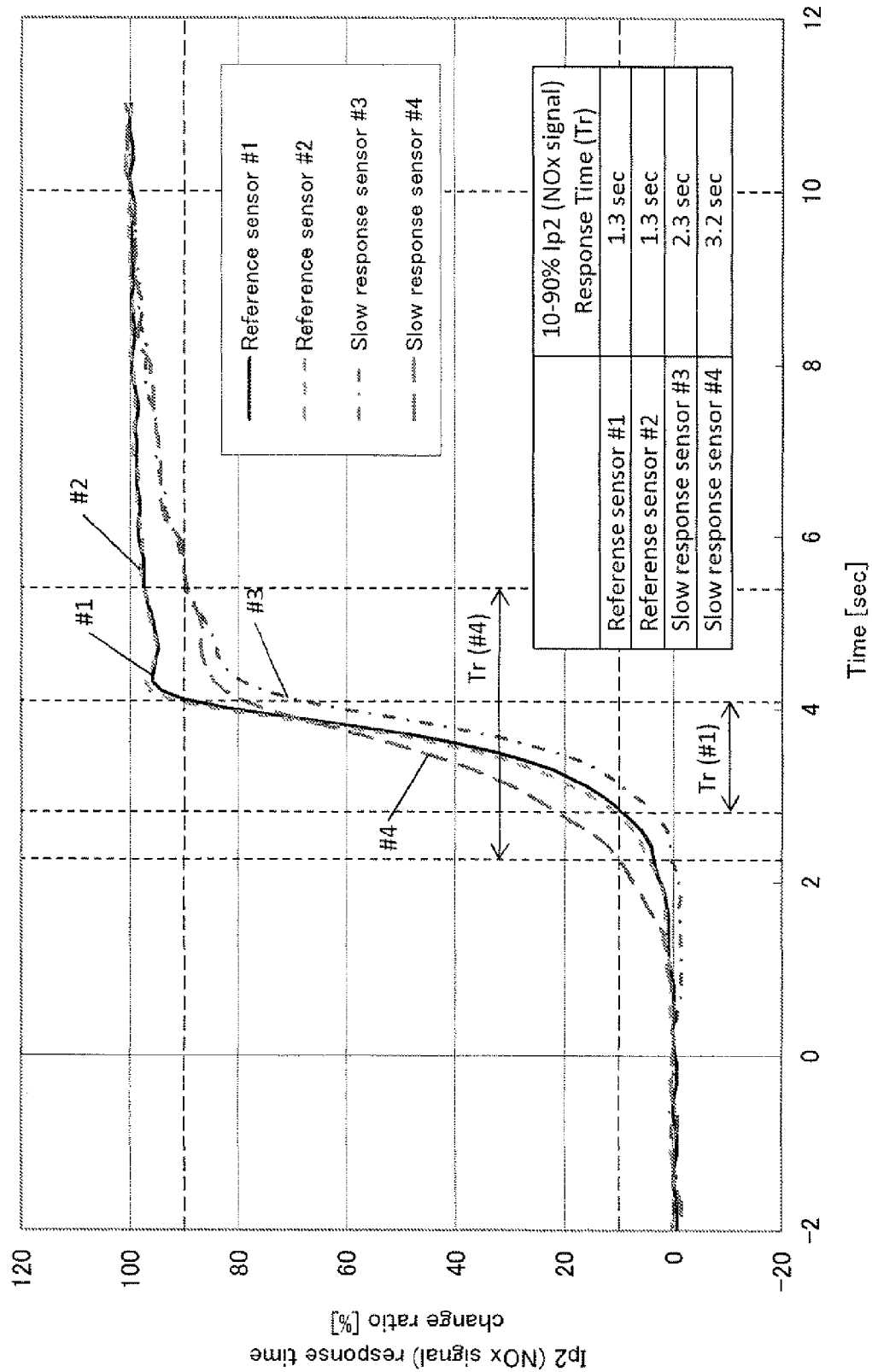
FIG. 3 is a graph showing the difference in a change in the second pump current due to a difference in the deterioration state of the NOx sensor element.

FIG. 3 is a graph showing, with the time axis expanded, the results of a test performed for four samples #1 to #4 of the NOx sensor element 10 so as to measure a change in the second pump current Ip2 when the target voltage Vr was changed as shown in FIG. 2. Samples #1 and #2 are NOx sensor elements which have not deteriorated (non-deteriorated products) and which serve as references. Samples #3 and #4 are NOx sensor elements which have deteriorated (deteriorated products). The vertical axis in FIG. 3 represents a relative current value (unit: %) on a scale determined such that the value of the second pump current Ip2 measured at time t=0 is taken as 0%, and the value of the second pump current Ip2 measured at time t=10 sec is taken as 100%. The value of the second pump current Ip2 measured when time t=0 (the relative current value is 0%) is equal to the initial value of the second pump current Ip2 (first concentration current to be described next). The value of the second pump current Ip2 measured when time t=10 sec (the relative current value is 100%) is approximately equal to a value to which the second pump current Ip2 converges after having changed (second concentration current to be described next).

As shown in FIG. 2, an operation of changing the target voltage Vr is started at time t=0 so as to change the target voltage Vr from the first target voltage Vr1 (=425 mV) to the second target voltage Vr2 (=225 mV) lower than the first target voltage Vr1 (period of time T of 4 sec from t=0 to t=4 sec). As a result, as shown in FIG. 3, the second pump current Ip2 changes; i.e., increases from the first concentration current (initial value: Ip2$a$ in FIG. 2) (the value in a state in which the target voltage Vr has become stable at the first target voltage Vr1) to the second concentration current (convergence value: Ip2$b$ in FIG. 2) (the value in a state in which the target voltage Vr has become stable at the second target voltage Vr2). Specifically, with a delay from the time when the target voltage Vr has started to change (time t=0), the second pump current Ip2 starts to increase at a point in time near the time t=1 sec, and sharply increases during a period between t=3 sec and t=4 sec. When the change of the target voltage Vr ends (t=4 sec), the second pump current Ip2 approaches the second concentration current (convergence value). As shown in FIG. 3, when Samples #3 and #4 whose deterioration has progressed are compared with Samples #1 and #2 which have not deteriorated, it is found that no large difference is present therebetween in terms of the behavior in a stage where the second pump current Ip2 increases sharply. However, in the case of Samples #3 and #4 whose deterioration has progressed, the period of time necessary for the second pump current Ip2 to approach the second concentration current becomes longer as compared with the case of Samples #1 and #2 which have not deteriorated. As can be understood from the above, the greater the degree of progress of deterioration of the NOx sensor element 10, the longer the period of time needed for the second pump current Ip2 to approach the second concentration current. Further, there is an appreciable difference in the length of this period due to a difference in the degree of deterioration. Therefore, if an index which reflects the length of this period is used, it becomes possible to determine the deterioration state of the NOx sensor element 10.

Next, an outline of a method of determining the deterioration state of the NOx sensor element 10 which is performed by the gas sensor controller 100 of the present embodiment will be described.

The gas sensor controller 100 of the present embodiment shown in FIG. 1 determines the deterioration state of the NOx sensor element 10 after the engine is stopped in response to an instruction from the ECU 90.

Upon start of the processing of determining the deterioration state of the NOx sensor element 10, as shown in FIG. 2, the gas sensor controller 100 changes the target voltage Vr for the concentration detection voltage Vs from the first target voltage Vr1 (=425 mV) for detection of NOx concentration to a second target voltage Vr2 (=225 mV) lower than the first target voltage Vr1. Notably, in the present embodiment, the target voltage Vr is changed rampwise at a gradient of −50 mV/sec from the first target voltage Vr1 (=425 mV) to the second target voltage Vr2 (=225 mV) over a period of time T of 4 sec.

As a result, as shown in FIG. 3, in each of Samples #1 to #4, the second pump current Ip2 increases from the first concentration current (initial value) which is the value when the target voltage Vr is the first target voltage Vr1 to the second concentration current (convergence value) which is the value when the target voltage Vr is the second target voltage Vr2. However, the length of the period required for the second pump current Ip2 to approach the second concentration current changes depending on the degree of deterioration of the NOx sensor element 10. In view of the above, in the present embodiment, the second pump current Ip2 when time t=0 (equal to the first concentration current) is taken as 0%, and the second pump current Ip2 when time t=10 sec (approximately equal to the second concentration current) is taken as 100%. A 10-90% response time Tr needed for the second pump current Ip2 to change from 10% to 90% is used for determining the deterioration state. The response time Tr serves as an index which represents or reflects the length of the period needed for the second pump current Ip2 to approach the second concentration current. Specifically, as shown in FIG. 3, whereas the response time Tr of each of Samples #1 and #2, which are non-deteriorated products, is 1.3 sec, the response times Tr of Samples #3 and #4, which are deteriorated products, are 2.3 sec and 3.2 sec, respectively. Therefore, the deteriorated products exhibit a longer response time Tr than the non-deteriorated products. In the case of Samples #1 and #2 (non-deteriorated products), the rate of increase of the second pump current Ip2 decreases gradually near the point where the second pump current Ip2 has reached 90%, and quickly converges to the second concentration current. In contrast, in the case of Samples #3 and #4 (deteriorated products), the rate of increase of the second pump current Ip2 decreases gradually near the point where the second pump current Ip2 has reached 70%, and slowly converges to the second concentration current.

Since the response time Tr of each deteriorated product includes a period in which the rate of increase of the second pump current Ip2 decreases gradually and the second pump current Ip2 approaches the second concentration current, the response time Tr becomes long (assumes a larger value). In contrast, since the response time Tr of each non-deteriorated product hardly includes the period in which the second pump current Ip2 approaches the second concentration current, the response time Tr becomes short (assumes a smaller value). Accordingly, the determination as to the deterioration state of the NOx sensor element 10 can be made by determining whether or not the 10-90% response time Tr is longer than a predetermined standard value (a deterioration determination time Tj to be described below).

In the present embodiment, the 10-90% response time Tr is used for making the deterioration determination. However, the index which reflects the length of the period needed for the second pump current Ip2 to approach the second concentration current is not limited thereto. For example, the embodiment may be modified to obtain the index (which reflects the length of the period needed for the second pump current Ip2 to approach the second concentration current) in a range different from the 10%-90% range (e.g., a 60-90% response time necessary for the second pump current Ip2 to change from 60% to 90%) and determine whether or not the NOx sensor element has deteriorated based on the length of the period. Alternatively, the embodiment may be modified to determine whether or not the NOx sensor element has deteriorated from the magnitude of the second pump current Ip2 at a predetermined time during the period during which the second pump current Ip2 approaches the second concentration current (for example, from the magnitude of the second pump current Ip2 at time t=5 sec). Alternatively, the embodiment may be modified to determine whether or not the NOx sensor element has deteriorated from the magnitude of the change (gradient) of the second pump current Ip2 during the period during which the second pump current Ip2 approaches the second concentration current (for example, a period between time t=5 sec and t=8 sec).

Next, in the gas sensor controller 100 of the present embodiment, the operation of the microprocessor 60 which realizes the above-described determination method will be described with reference to the flowcharts of FIG. 4 and FIGS. 5A and 5B.

Figure 4:
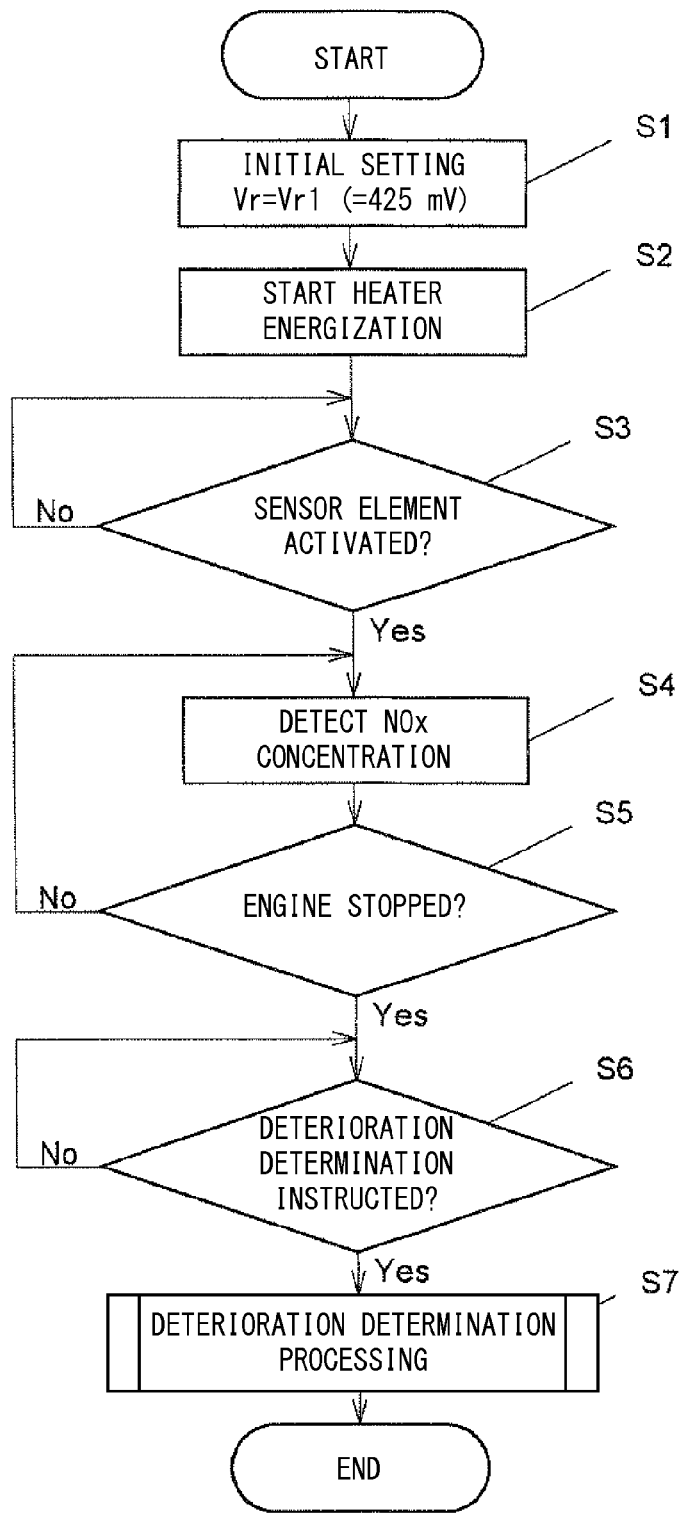
FIG. 4 is a flowchart showing the processing operation of a microprocessor of the gas sensor controller according to the embodiment.
Figure 5A:
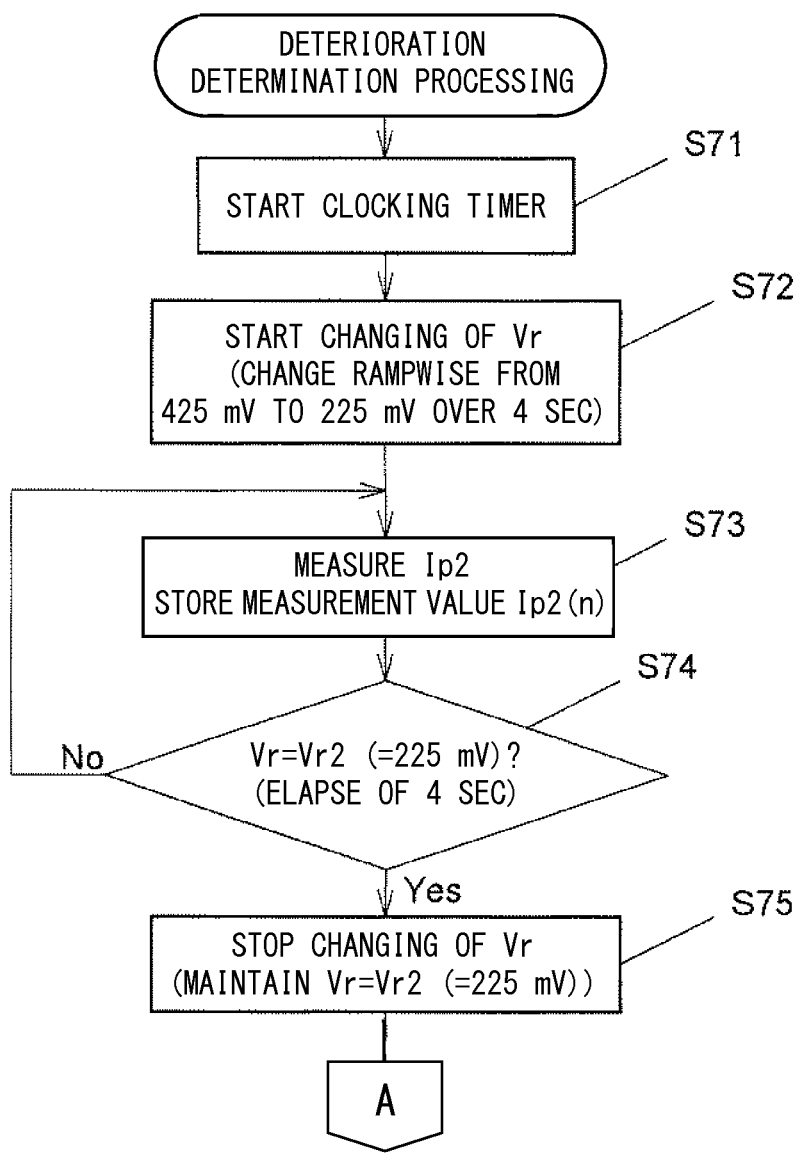
FIGS. 5A and 5B are flowcharts of a deterioration determination routine according to the embodiment.
Figure 5B:
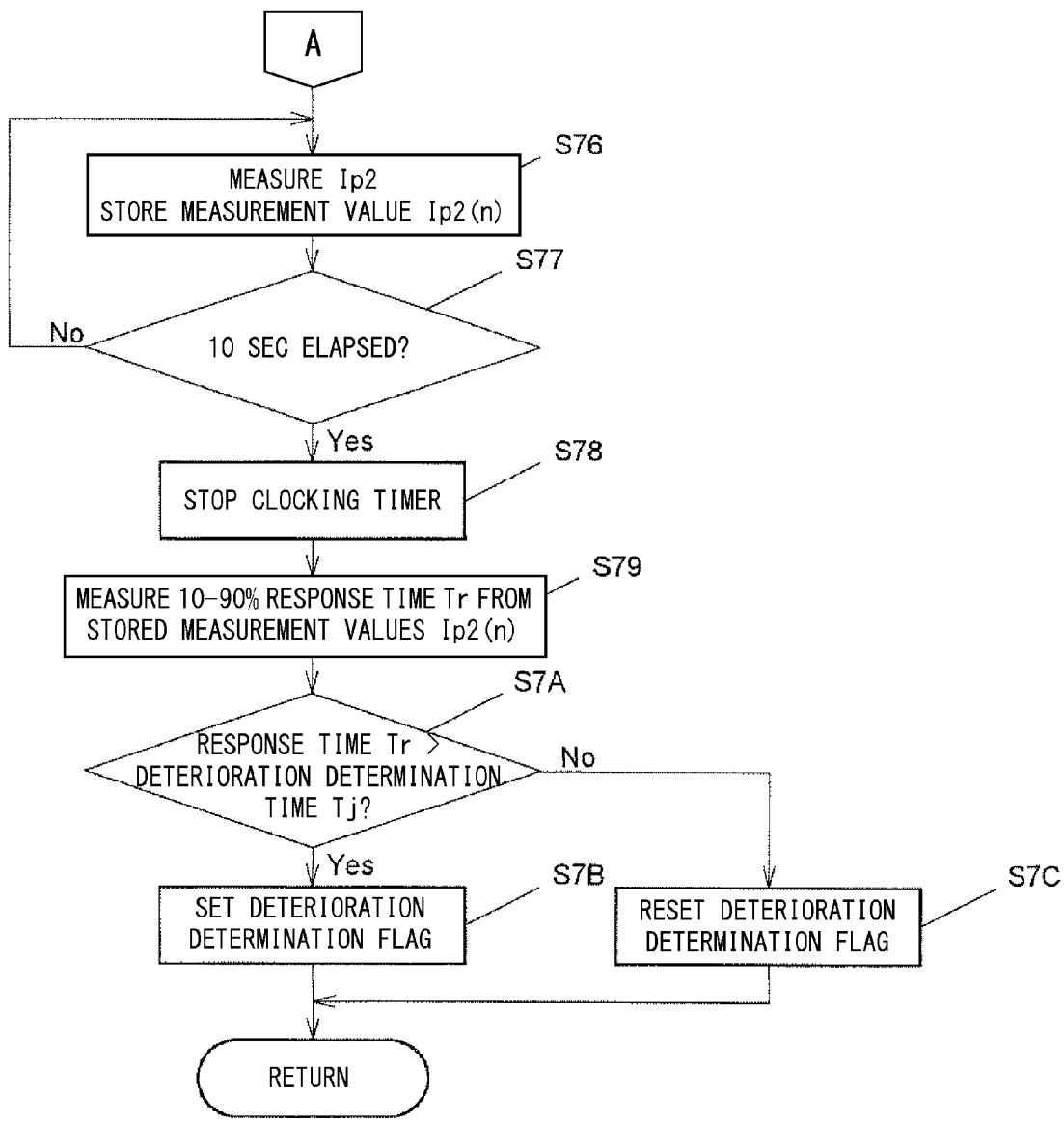

As shown in FIG. 4, when the engine is started and the microprocessor 60 of the gas sensor controller 100 starts processing, the microprocessor 60 first performs various initial settings in step S1, and sets the target voltage Vr (which is compared in the reference voltage comparison circuit 51 with the concentration detection voltage Vs detected by the Vs detection circuit 53) to the first target voltage Vr1 (=425 mV) for detection of NOx concentration (see FIG. 2).

Next, in step S2, the microprocessor 60 instructs the heater drive circuit 57 to start the supply of electric current to the heater section 180.

In step S3 subsequent thereto, the microprocessor 60 determines whether or not the NOx sensor element 10 has been activated. In the case where the NOx sensor element 10 has not yet been activated (No), the microprocessor 60 repeatedly performs the processing of step S3 so as to wait until the NOx sensor element 10 becomes active. When the NOx sensor element 10 becomes active and the microprocessor 60 makes a "Yes" determination in step S3, the microprocessor 60 proceeds to step S4.

In step S4, the microprocessor 60 detects the NOx concentration. In step S5 subsequent thereto, the microprocessor 60 obtains from the ECU 90 information indicating whether or not the engine is stopped. In the case where the engine is not in a stopped state, the microprocessor 60 makes a "No" determination in step S5, and repeats the above-mentioned steps S4 and step S5 so as to continue the detection of NOx concentration.

When the engine is stopped and the microprocessor 60 makes a "Yes" determination in step S5, the microprocessor 60 proceeds to step S6.

In step S6, the microprocessor 60 determines whether or not an instruction of deterioration determination is output from the ECU 90. In the case where the instruction of deterioration determination is not output (No), the microprocessor 60 repeats step S6 so as to wait until the instruction of deterioration determination is output. When the instruction of deterioration determination is output (Yes), the microprocessor 60 proceeds to step S7 so as to execute a deterioration determination processing routine (which includes step S71 and steps subsequent thereto shown in FIGS. 5A and 5B). Subsequently, the microprocessor 60 ends the processing shown in FIG. 4.

Next, the deterioration determination processing routine of FIGS. 5A and 5B will be described.

First, in step S71, the microprocessor 60 starts a clocking timer which measures a processing lapse time using an internal timer (not shown).

Next, in step S72, the microprocessor 60 starts to change the target voltage Vr, which is compared with the concentration detection voltage Vs in the reference voltage comparison circuit 51. Here, the microprocessor 60 changes the target voltage Vr rampwise at a gradient of −50 mV/sec from the first target voltage Vr1 (=425 mV) for detection of NOx concentration to the second target voltage Vr2 (=225 mV) lower than the first target voltage Vr1 over a period of time T of 4 sec.

Next, in step S73, the microprocessor 60 measures the second pump current Ip2 using the Ip2 detection circuit 55, and stores the measurement value Ip2(n=1) (n is a natural number) of the second pump current Ip2 in a memory (not shown) provided in the microprocessor 60.

In step S74 subsequent thereto, the microprocessor 60 determines whether or not the target voltage Vr has reached the second target voltage Vr2 (=225 mV). In the case where the target voltage Vr has not yet reached the second target voltage Vr2 (=225 mV), the microprocessor 60 makes a "No" determination in step S74 and returns to step S73 so as to repeat the operation of measuring the second pump current Ip2 and storing its measurement value Ip2(n) in the memory.

When the target voltage Vr has reached the second target voltage Vr2 (=225 mV), i.e., when 4 sec has elapsed after the start of the clocking timer and the start of the operation of changing the target voltage Vr (time t=4 sec), the microprocessor 60 makes a "Yes" determination in step S74, and proceeds to step S75.

In step S75, the microprocessor 60 stops the operation of changing the target voltage Vr. After that, the target voltage Vr is maintained at the second target voltage Vr2 (=225 mV).

Next, the microprocessor 60 proceeds to step S76 and measures the second pump current Ip2 using the Ip2 detection circuit 55, and stores its measurement value Ip2(n) in the memory as in the above-described step S74.

In step S77 subsequent thereto, the microprocessor 60 determines whether or not 10 sec has elapsed after the start of the clocking timer. In the case where 10 sec has not yet elapsed after the start of the clocking timer, the microprocessor 60 returns to step S76 so as to repeat the operation of measuring the second pump current Ip2 and storing its measurement value Ip2(n) in the memory until 10 sec has elapsed.

When 10 sec has elapsed after the start of the clocking timer (time t=10 sec), the microprocessor 60 makes a "Yes" determination in step S77, and proceeds to step S78 so as to stop the clocking timer and stop the measurement of the second pump current Ip2. Namely, the microprocessor 60 interrupts the measurement of the second pump current Ip2 at time t=10 sec.

Next, in step S79, the microprocessor 60 converts the stored measurement vales Ip2(n) to relative values under the condition that the initial measurement value Ip2(n=1) of the second pump current Ip2 (time t=0) is taken as 0% (equal to the first concentration current) and the measurement value Ip2(n=N) of the second pump current Ip2 after elapse of 10 sec (time t=10 sec) is taken as 100% (approximately equal to the second concentration current). The microprocessor 60 then obtains, from the relative value of each measurement value Ip2(n), a 10-90% response time Tr necessary for the second pump current Ip2 to change from 10% to 90% (see FIG. 3). As described above, this response time Tr serves as an index which reflects the length of the period over which the second pump current Ip2 approaches the second concentration current. The greater the degree of deterioration of the NOx sensor element 10, the longer the response time Tr.

In step S7A subsequent to S79, the microprocessor 60 determines whether or not the obtained response time Tr is longer than the predetermined deterioration determination time Tj (Tj=2.0 sec in the present embodiment). In the case where the response time Tr is longer than the deterioration determination time Tj, the microprocessor 60 makes a "Yes" determination in step S7A, and proceeds to step S7B. In step S7B, the microprocessor 60 determines that the NOx sensor element 10 is in a deteriorated state, and sets a deterioration determination flag. Meanwhile, in the case where the microprocessor 60 makes a "No" determination in step S7A, the microprocessor 60 proceeds to step S7C. In step S7C, the microprocessor 60 determines that the NOx sensor element 10 is not in a deteriorated state, and resets the deterioration determination flag.

After the above-mentioned step S7B or step S7C, the microprocessor 60 ends the deterioration determination processing routine.

In the case where the microprocessor 60 sets the deterioration determination flag in step S7B, the microprocessor 60 reports to the ECU 90 the fact that the NOx sensor element 10 is in a deteriorated state. The ECU 90 performs a predetermined warning process; for example, the ECU 90 notifies a user of the reported deteriorated state and prompts the user to replace the NOx sensor 20.

In the present embodiment, the NOx sensor element 10 corresponds to the gas sensor element of the present invention, and the NOx sensor 20 corresponds to the gas sensor. The second-pump-dedicated first electrode 145 corresponds to the first electrode, and the second-pump-dedicated second electrode 147 corresponds to the second electrode. The second pump current Ip2 corresponds to the concentration current, and the concentration detection voltage Vs corresponds to the concentration voltage.

The reference voltage comparison circuit 51, the Ip1 drive circuit 52, and the Vs detection circuit 53 correspond to the first chamber control means, and the microprocessor 60 which executes steps S72 and S75 corresponds to the target voltage changing means. The Ip2 detection circuit 55 and the microprocessor 60 which executes steps S73 and S76 correspond to the current detection means.

The microprocessor 60 which executes the deterioration determination processing routine of step S7 (step S71 and steps subsequent thereto) corresponds to the deterioration determination means.

As described above, in the gas sensor controller 100 of the present embodiment, the first chamber control means (the reference voltage comparison circuit 51, the Ip1 drive circuit 52, and the Vs detection circuit 53) pumps oxygen out of or into the first measurement chamber MR1 using the first pump cell 111 such that the concentration detection voltage Vs becomes equal to the target voltage Vr. Meanwhile, the target voltage changing means (step S72) changes the target voltage Vr for the concentration detection voltage Vs from the first target voltage Vr1 to the second target voltage Vr2. The current detection means (the Ip2 detection circuit 55 and steps S73 and S76) detects the magnitude of the second pump current Ip2 (concentration current) flowing between the second-pump-dedicated first electrode 145 (the first electrode) and the second-pump-dedicated second electrode 147 (the second electrode) of the second pump cell 113. When the target voltage Vr for the concentration detection voltage Vs is changed, the oxygen concentration of the first chamber gas GM1 changes, and the concentrations of oxygen molecules and oxygen-containing gas of the second chamber gas GM2 within the second measurement chamber MR2 also change. Therefore, the magnitude of the detected second pump current Ip2 (concentration current) also changes. The way in which the second pump current Ip2 changes depends on the degree of deterioration of the NOx sensor element 10. Therefore, the deterioration determination means (step S7) can determine the deterioration state of the NOx sensor element 10 from a change in the second pump current Ip2 which in turn occurs as a result of a change in the target voltage Vr for the concentration detection voltage Vs.

Notably, in the present embodiment, the target voltage Vr for the concentration detection voltage Vs is changed from the first target voltage Vr1 (=425 mV), which is maintained when the NOx concentration is detected, to the second target voltage Vr2 (=225 mV) lower than the first target voltage Vr1. As a result, the second pump current Ip2 increases, and its rate of increase then decreases gradually. The second pump current Ip2 then approaches a predetermined current value. At that time, the greater the degree of deterioration of the NOx sensor element 10, the longer the period necessary for the second pump current Ip2 to approach the predetermined current value. Therefore, in the present embodiment, the deterioration determination is performed using the response time Tr which relates to the change occurring in the second pump current Ip2 and reflects the length of the above-mentioned period during which the second pump current Ip2 changes to approach the predetermined current value.

Also, in the gas sensor controller 100 of the present embodiment, the target voltage Vr for the concentration detection voltage Vs is changed from the first target voltage Vr1 to the second target voltage Vr2. This makes it possible to obtain a change in the second pump current Ip2 (concentration current) and to determine the deterioration state of the NOx sensor element 10.

Further, in the gas sensor controller 100 of the present embodiment, the target voltage changing means changes the target voltage Vr gradually (rampwise in the present embodiment) from the first target voltage Vr1 (=425 mV) to the second target voltage Vr2 (=225 mV) over a period of time T of 4 sec (see FIG. 2). Since the target voltage Vr is changed gradually over a predetermined period of time, the obtained second pump current Ip2 (concentration current) does not overshoot, and a change in the second pump current Ip2 corresponding to the deterioration state of the NOx sensor element 10 can be obtained.

In the above, the gas sensor controller, the gas sensor system, and the method for determining the deterioration of the gas sensor element according to the present invention have been described based on the gas sensor controller 100 and the NOx sensor system 1 of the embodiment. However, the present invention is not limited to the above-described embodiment, and may be freely modified without departing from the scope of the invention.

For example, in the embodiment, in response to an instruction from the ECU 90, the deterioration state of the NOx sensor element 10 is determined after the engine has stopped. After the target voltage Vr that is compared with the concentration detection voltage Vs is changed from the first target voltage Vr1 for detection of NOx concentration to the second target voltage Vr2, the target voltage Vr may be returned to the first target voltage Vr1 so as to continue the detection of NOx concentration.

However, the deterioration determination may be performed during the period of idling stop or fuel cut. In this case, in order to resume the detection of NOx concentration after performing the deterioration determination by changing the target voltage Vr from the first target voltage Vr1 to the second target voltage Vr2, the target voltage Vr is returned to the first target voltage Vr1 after completing the deterioration determination as shown in the period between time t=16 sec and time t=20 sec of FIG. 2.

In the embodiment, after stopping the engine, the deterioration state of the NOx sensor element 10 is determined in accordance with an instruction from the ECU 90. However, the gas sensor controller 100 may independently perform the deterioration determination without receiving any instruction from the ECU 90. Namely, in the embodiment, the gas sensor controller 100 waits for an instruction from the ECU 90 after the engine has been stopped, and determines the deterioration state of the NOx sensor element 10 every time it receives the instruction. However, the gas sensor controller 100 may independently perform the deterioration determination every time the engine has stopped a predetermined number of times (e.g., 10 times) or at predetermined intervals (e.g., once a month).

In the embodiment, the 10-90% response time Tr needed for the second pump current Ip2 to change from 10% to 90% is obtained under the condition that the initial measurement value Ip2(n=1) of the second pump current Ip2 (time t=0) (equal to the first concentration current) is taken as 0%, and the measurement value Ip2(n=N) of the second pump current Ip2 at time t=10 sec (approximately equal to the second concentration current) is taken as 100%; and the deterioration determination is performed based on the response time Tr. However, as described above, the deterioration determination may be performed using any of other indexes which reflect the length of the period needed for the second pump current Ip2 (concentration current) to approach the second concentration current, for example, a 60-90% response time necessary for the second pump current Ip2 to change from 60% to 90%, the magnitude of the second pump current Ip2 at time t=5 sec, and the magnitude of the change (gradient) of the second pump current Ip2 during the period between time t=5 sec and t=8 sec.

In the embodiment, the target voltage Vr is changed rampwise from the first target voltage Vr1 to the second target voltage Vr2 over a period of time T of 4 sec. However, the method of changing the target voltage Vr and the period of the change may be freely modified. For example, instead of changing the target voltage Vr rampwise, the target voltage Vr may be changed to exhibit an S-shaped change such that its rate of change is small at the beginning and end of the change and the rate of change is large at the middle of the change. Alternatively, the target voltage Vr may be changed instantaneously from the first target voltage Vr1 to the second target voltage Vr2 or may be changed stepwise with the elapse of time.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

What is claimed is:

1. A gas sensor controller for controlling a gas sensor element having a first measurement chamber into which an external object gas is introduced and a second measurement chamber which communicates with the first measurement chamber and into which a first chamber gas within the first measurement chamber is introduced, the gas sensor element comprising:
   a first pump cell which is formed of a first solid electrolyte body and which pumps oxygen out of the first chamber gas within the first measurement chamber or pumps oxygen into the first measurement chamber;
   a second pump cell which is formed of a second solid electrolyte body and which has first and second electrodes formed on the second solid electrolyte body such that the first electrode is located in the second measurement chamber and the second electrode is located outside the second measurement chamber; and
   an oxygen concentration detection cell which is formed of a third solid electrolyte body and which has detection and reference electrodes formed on the third solid electrolyte body such that the detection electrode is located in the first measurement chamber and the reference electrode is exposed to an atmosphere having a reference oxygen concentration,
   wherein
   the gas sensor controller comprises:
   first chamber control means for pumping oxygen out of the first measurement chamber or pumping oxygen into the first measurement chamber by operating the first pump cell such that a concentration voltage generated between the detection electrode and the reference electrode of the oxygen concentration detection cell becomes equal to a target voltage;
   target voltage changing means for changing the target voltage from a first target voltage to a second target voltage different from the first target voltage;
   current detection means for detecting a magnitude of a concentration current which flows between the first electrode and the second electrode in accordance with a concentration of oxygen molecules and oxygen-containing gas molecules having a dissociation voltage higher than that of oxygen molecules, the oxygen molecules and the oxygen-containing gas molecules being contained in a second chamber gas within the second measurement chamber; and
   deterioration determination means for determining a deterioration state of the gas sensor element from a change which occurs in the concentration current as a result of the target voltage being changed by the target voltage changing means,
   wherein the target voltage changing means gradually changes the target voltage from the first target voltage to the second target voltage such that the concentration current does not overshoot.

2. The gas sensor controller as claimed in claim 1, wherein in the case where the second target voltage is lower than the first target voltage, and the concentration current increases from a first concentration current to a second concentration current as a result of the target voltage being changed from the first target voltage to the second target voltage by the target voltage changing means, the deterioration determination means determines the deterioration state of the gas sensor element based on an index which relates to the change occurring in the concentration current and reflects the length of a period needed for the concentration current to approach the second concentration current.

3. A gas sensor system which includes a gas sensor controller as claimed in claim 1 and a gas sensor including the gas sensor element and which is mounted on a vehicle, wherein the deterioration determination means of the gas sensor controller determines the deterioration state of the gas sensor element after an engine of the vehicle is stopped.

4. A deterioration determination method for determining a deterioration state of a gas sensor element having a first measurement chamber into which an external object gas is introduced and a second measurement chamber which communicates with the first measurement chamber and into which a first chamber gas within the first measurement chamber is introduced, the gas sensor element comprising:
   a first pump cell which is formed of a first solid electrolyte body and which pumps oxygen out of the first chamber gas within the first measurement chamber or pumps oxygen into the first measurement chamber;
   a second pump cell which is formed of a second solid electrolyte body and which has first and second electrodes formed on the second solid electrolyte body such that the first electrode is located in the second measurement chamber and the second electrode is located outside the second measurement chamber; and
   an oxygen concentration detection cell which is formed of a third solid electrolyte body and which has detection and reference electrodes formed on the third solid electrolyte body such that the detection electrode is located in the first measurement chamber and the reference electrode is exposed to an atmosphere having a reference oxygen concentration, wherein the method comprises the steps of:
   creating a state in which oxygen is pumped out of the first measurement chamber or is pumped into the first measurement chamber by the first pump cell such that a concentration voltage generated between the detection electrode and the reference electrode of the oxygen concentration detection cell becomes equal to a target voltage which is set to a first target voltage;
   changing the target voltage from the first target voltage to a second target voltage different from the first target voltage;
   detecting a concentration current which flows between the first electrode and the second electrode in accordance with a concentration of oxygen molecules and oxygen-containing gas molecules having a dissociation voltage higher than that of oxygen molecules, the oxygen molecules and the oxygen-containing gas molecules being contained in a second chamber gas within the second measurement chamber; and
   determining the deterioration state of the gas sensor element from a change which occurs in the concentration current as a result of a change in the target voltage,
   wherein the target voltage is gradually changed from the first target voltage to the second target voltage such that the concentration current does not overshoot.

5. The deterioration determination method according to claim 4, wherein in the case where the second target voltage is lower than the first target voltage, and the concentration current increases from a first concentration current to a second concentration current as a result of the target voltage being changed from the first target voltage to the second target voltage, the deterioration state is determined based on an index which relates to the change occurring in the concentration current and reflects the length of a period needed for the concentration current to approach the second concentration current.

6. The gas sensor controller as claimed in claim 5, wherein the index is compared to a predetermined time period.

7. The gas sensor controller as claimed in claim 6, wherein, when the index is greater than the predetermined time period, the deterioration determination means determines that the sensor is in a deteriorated state.

8. The method as claimed in claim 2, wherein the index is compared to a predetermined time period.

9. The method as claimed in claim 8, wherein, when the index is greater than the predetermined time period, the sensor is determined to be in a deteriorated state.

* * * * *